United States Patent [19]

Daly

[11] Patent Number: 5,567,679
[45] Date of Patent: Oct. 22, 1996

[54] USE OF CGRP IN TREATING ALOPECIA

[76] Inventor: Theodore J. Daly, 200 East Ave., Hicksville, N.Y. 11801

[21] Appl. No.: 430,505

[22] Filed: Apr. 28, 1995

Related U.S. Application Data

[63] Continuation-in-part of Ser. No. 165,185, Dec. 13, 1993, abandoned.

[51] Int. Cl.$^6$ .................................................. A61K 38/23
[52] U.S. Cl. ................... 514/12; 514/9; 514/11
[58] Field of Search ....................... 514/12, 11, 9; 530/307, 324

[56] References Cited

U.S. PATENT DOCUMENTS

| | | | |
|---|---|---|---|
| 4,530,838 | 7/1985 | Evans et al. | 514/11 |
| 4,992,530 | 2/1991 | Morita et al. | 530/307 |
| 5,049,654 | 9/1991 | Morita et al. | 530/307 |
| 5,214,030 | 5/1993 | Stief | 514/12 |

OTHER PUBLICATIONS

Smith et al., Cutaneous responses to vasoactive . . . , *Lancet* 1992; vol. 339, pp. 91–93.

Nong et al., Peptides Encoded by Calcitonin . . . , J. Immun.; vol. 143; pp. 45–49; 1989.

Foreman, Substance P and Calcitonin . . . ; Int. Archs. Allergy appl., Innun.; vol 82, pp. 366–371, 1987.

Bunker et al., Calcitonin gene–related peptide . . . , Lancet, vol. 342, pp. 80–82, 1993.

Jernbeck et al., Calcitonin gene–related peptide . . . , Plast. Reconstr. Surg., vol. 91, pp. 245–251, 1993.

Jernbeck et al., The effect of calcitoning . . . , Clinical Phys. vol. 10, pp. 335–343, 1990.

Jernbeck et al., Calcitonin gene—related peptide . . . , Plast. Reconstr. Surg. vol. 91, pp. 236–244, 1993.

*Primary Examiner*—Howard E. Schain
*Attorney, Agent, or Firm*—Dilworth & Barrese

[57] ABSTRACT

The present invention relates to the use of Calcitonin Gene Related Peptide (CGRP), either topically or intramuscularly, as a treatment for hair loss. The use of calcitonin or CGRP, either topically or intramuscularly, for hair loss includes the steps of preparing a liquid carrier, adding calcitonin to the carrier, injecting the mixture into a subject intramuscularly, intravascularly, intradermally or subcutaneously, and analyzing results on the subject.

11 Claims, No Drawings

USE OF CGRP IN TREATING ALOPECIA

CONTINUING DATA

This is a continuation-in-part of application Ser. No. 08/165,185 filed Dec. 13, 1993 and now abandoned.

BACKGROUND OF THE INVENTION

1. Field of the Invention

The present invention relates to the use of calcitonin and calcitonin gene-related peptide (CGRP) for treating hair loss. More particularly, the present invention relates to the use of CGRP either topically or intramuscularly as a treatment for alopecia areata or hair loss.

2. Description of the Prior Art

Alopecia areata is a disease with no known cause. Thyroid abnormalities are associated with the disease in about 10% of the cases. Thyroid supplement does not cause hair regrowth in alopecia areata patients.

A thyroid produced hormone, namely calcitonin, discovered in 1962, has not been measured in alopecia areata patients except in one unpublished study where the levels were found to be significantly lower than "normal".

Calcitonin levels are elevated in pregnancy. Female alopecia areata patients often experience hair regrowth during pregnancy. Women who are not afflicted with alopecia areata often experience luxurious hair growth during pregnancy. The increase in-hair growth in both normal individuals and alopecia areata patients during pregnancy appears to be due to increased levels of calcitonin.

One theory of the cause of alopecia areata is that it is an autoimmune disorder in which the body's cells attack the hair. It has been shown that CGRP reduces langerhans cell activity, i.e., cells that are involved in autoimmune responses.

Numerous innovations for methods for treating hair loss have been provided in the prior art. Even though these innovations may be suitable for the specific individual purposes to which they address, they would not be suitable for the purposes of the present invention as heretofore described.

SUMMARY OF THE INVENTION

Accordingly, it is an object of the present invention to provide a treatment for hair loss.

More particularly, it is an object of the present invention to provide a treatment for hair loss that avoids the disadvantages of the prior art.

Calcitonin is a hormone with no known deficiency state. Elevations occur in thyroid cancer among other disease states. A preliminary study of calcitonin levels of 15 alopecia areata and 15 "normal" subjects was performed and showed a statistically significant lower level in alopecia areata patients.

In keeping with these objects, and with others which will become apparent hereinafter, one feature of the present invention resides, briefly stated, in a treatment for hair loss including the steps of, preparing a liquid carrier, adding Calcitonin Gene Related Peptide (CGRP) to the carrier, injecting the composition into a subject intramuscularly, subcutaneously, or intradermally wherein the results were analyzed.

In keeping with these objects, and with others which will become apparent hereinafter, another feature of the present invention resides, briefly stated, in a treatment for hair loss including the steps of preparing a topical carrier, adding CGRP to the carrier, applying the mixture topically to the subject wherein the results were analyzed.

The novel features which are considered characteristic for the invention are set forth in particular in the appended claims. The invention itself, however, both as to its construction and its method of operation, together with additional objects and advantages thereof, will be best understood from the following description of the specific embodiments when read in connection with the accompanying drawing.

DETAILED DESCRIPTION OF THE PREFERRED EMBODIMENT

Calcitonin levels are decreased in alopecia areata patients and this contributes to, or is the direct cause of, the hair loss.

Calcitonin controls or plays a part in controlling the superficial cutaneous circulation. A transient or prolonged deficiency or absence of calcitonin causes impaired cutaneous circulation with subsequent impaired or absent hair growth.

The presence of thyroid disease or abnormalities in 10% of alopecia areata patients has never been adequately explained. The reason for this is that calcitonin has never been measured and that the usual thyroid parameters, though abnormal, are only indirectly associated with a thyroid abnormality that manifests itself in a calcitonin deficiency with resulting alopecia areata. This may be why only 10% show abnormalities. The wrong thyroid hormone may have been measured.

It is believed that calcitonin gene-related peptide (CGRP) is the protein that is missing or deficient in some, if not all, cases of hair loss diseases such as alopecia areata. CGRP was recently described in the early 1980's and is obtained through alternative processing of the gene encoding calcitonin, a well known protein product of the thyroid gland. Alopecia areata can cause temporary patchy hair loss or total hair loss of the whole body including pubic hair and underarm hair. The cause of alopecia areata is unknown.

A high percentage (13–80+%) of patients having alopecia areata have demonstrable thyroid disease. CGRP is produced by the thyroid. Thus, it appears that thyroid gland disease results in decreased CGRP and hence increased hair loss.

Stress seems to precipitate attacks of alopecia areata. Numerous studies show that CGRP is decreased in subjects that under stress.

CGRP is a potent vasodilator that increases superficial circulation and enhances blood vessel formation. It is logical that a deficiency of CGRP would decrease the flow of blood to the superficial circulation, decrease blood vessel formation, and cause hair loss.

Alopecia areata is associated with 10% or more of eczema cases, which is another disease of unknown cause that may be caused by decreased superficial blood flow. About 4% of Vitiligo is also associated with alopecia areata. Vitiligo is another disease of unknown cause where a loss of pigment cells in the skin causes white patches. The loss of pigment cells in the skin appears to be due to decreased blood flow.

Since alopecia areata patients are also known to have decreased sweat production, CGRP appears to be involved in controlling the superficial circulation and skin appendages such as sweat glands and the hair.

The present invention employs CGRP in conjunction with a pharmaceutically acceptable carrier to ameliorate or reverse hair loss. Pharmaceutically acceptable carriers suitable for use with the present invention include biocompatible solutions, creams, gels, ointments, etc. Preferably, the carrier includes saline solution and water.

The composition described herein can be injected into a subject intramuscularly, subcutaneously or intradermally. Alternatively, the composition can be applied topically to a subject or administered intranasally.

EXAMPLE 1

Comparison of Calcitonin Levels in Alopecia Areata Patients and Control Patients Table 1, infra, is the results of the calcitonin levels in two groups of 15 patients each - one group with alopecia areata, and another group as a control.

TABLE 1

| PATIENT | ALOPECIA AREATA | NOT ALOPECIA AREATA (CONTROL) |
|---|---|---|
| 1 | 4.4 | 25 |
| 2 | 29.4 | 31 |
| 3 | 30 | 35 |
| 4 | 33.3 | 39.8 |
| 5 | 33.3 | 40 |
| 6 | 33.3 | 45.4 |
| 7 | 37.1 | 52.4 |
| 8 | 38.2 | 54.8 |
| 9 | 38.4 | 56.7 |
| 10 | 40 | 57.7 |
| 11 | 41.1 | 58.1 |
| 12 | 42.1 | 59.6 |
| 13 | 45.9 | 60 |
| 14 | 50 | 65.3 |
| 15 | 96.7 | 67.9 |
| MEAN | 39.547 | 49.913 |
| STANDARD DEVIATION | 18.862 | 13.042 |

EXAMPLE 2

Preparation of CGRP Solution

Human cyclic CGRP was obtained from Bachem Labs of Torrence, Cal. 0.5 mg of the CGRP was mixed in 1 cc of sterile water. The CGRP and water mixture was then injected into 24 cc of 0.9% saline solution through a 0.2 micron millipore filter to form a first solution having a concentration of 20 micrograms/ml. One milliliter of the first solution was added to 19 cc of saline solution to form a second solution having a final concentration of 1 microgram/ml or 0.1 microgram/0.1 ml.

EXAMPLE 3

Administration of Calcitonin Gene-Related Peptide (CGRP) to an Alopecia Areata Patient A 1 cc syringe having a 30 gauge needle was used to intradermally inject 0.3 ml of the second solution (0.1 microgram/0.1 ml) of Example 2 to an affected area two or three times per day. Hair growth will occur in the affected area.

EXAMPLE 4

Topical Administration of CGRP to an Alopecia Areata Patient 0.3 ml of the second solution of Example 2 was diluted in 1 cc of dimethylsulfoxide (DMSO) and topically applied to a 2 cm area of the epidermis of an alopecia areata patient. Hair growth will occur in the affected area.

It will be understood that each of the elements described above, or two or more together, may also find a useful application in other types of constructions differing from the type described above.

While the invention has been illustrated and described as embodied in the use of calcitonin either topically or intramuscularly as a treatment for hair loss, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A method for treating a subject having alopecia which comprises:

providing a pharmaceutically acceptable carrier;

adding CGRP to the carrier to form a composition;

introducing the composition into a subject to increase superficial cutaneous circulation in the subject thereby increasing hair growth in the subject.

2. A method according to claim 1, wherein said carrier is selected from the group consisting of saline solution, water and mixtures thereof.

3. A method according to claim 1, wherein said step of introducing said composition into a subject includes introducing about greater than 0.3 ml of said composition into said patient, wherein said concentration of said composition is about 0.1 microgram CGRP per 0.1 ml of said carrier.

4. A method according to claim 3, wherein said step of introducing said composition into a subject is performed from about two to about three times per day.

5. A method according to claim 5, wherein said step of introducing said composition into said subject includes intranasal introduction of said composition into said subject.

6. A method for treating a subject having alopecia which comprises:

providing a pharmaceutically acceptable carrier;

adding CGRP to the carrier to form a composition;

applying the composition topically to the subject to increase superficial cutaneous circulation in said subject thereby increasing hair growth in said subject.

7. A method according to claim 6, wherein said carrier is selected from the group consisting of saline solution, water and mixtures thereof.

8. A method according to claim 6, further comprising the step of diluting the composition in a solvent prior to application of the composition to the subject.

9. A method according to claim 8, wherein said solvent is dimethylsulfoxide.

10. A method according to claim 8, wherein about 0.3 mls of said composition having a concentration of about 1 microgram of CGRP per milliliter of carrier is diluted in 1 cc of dimethylsulfoxide.

11. A method according to claim 10, wherein said step of applying said composition to a subject includes application of the composition to said subject about two times per day.

* * * * *